US011540865B2

(12) United States Patent
Ghobadi et al.

(10) Patent No.: US 11,540,865 B2
(45) Date of Patent: *Jan. 3, 2023

(54) CONTOURABLE PLATE (71) Applicant: Zimmer Biomet CMF and Thoracic, LLC, Jacksonville, FL (US)

(72) Inventors: Shahin Ghobadi, Fort Lee, NJ (US); Saddy Garcia, St. Augustine, FL (US); Adam Hausman, Jacksonville, FL (US); Shawn Robinson, Fleming Island, FL (US); Max Holland Billard, Jacksonville, FL (US); Ryan N Luby, Ponte Vedra Beach, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 396 days.

This patent is subject to a terminal disclaimer.

(21) Appl. No.: 16/707,561

(22) Filed: Dec. 9, 2019

(65) Prior Publication Data

US 2020/0188000 A1    Jun. 18, 2020

Related U.S. Application Data

(63) Continuation of application No. 14/530,902, filed on Nov. 3, 2014, now Pat. No. 10,531,900.

(Continued)

(51) Int. Cl.
*A61B 17/80* (2006.01)
*A61B 17/86* (2006.01)
*A61B 17/68* (2006.01)

(52) U.S. Cl.
CPC ...... *A61B 17/8071* (2013.01); *A61B 17/8023* (2013.01); *A61B 17/8085* (2013.01); *A61B 17/863* (2013.01); *A61B 2017/681* (2013.01)

(58) Field of Classification Search
CPC ............ A61B 17/8071; A61B 17/8076; A61B 17/8085; A61B 17/8004; A61B 17/8019;
(Continued)

(56) References Cited

U.S. PATENT DOCUMENTS 6,575,741 B2    6/2003  Campbell
6,730,091 B1 *  5/2004  Pfefferle .............. A61B 17/863
                                                           606/291

(Continued)

OTHER PUBLICATIONS

"U.S. Appl. No. 14/530,902, Advisory Action dated Nov. 27, 2017", 3 pgs.

(Continued)

*Primary Examiner* — Amy R Sipp
(74) *Attorney, Agent, or Firm* — Schwegman Lundberg & Woessner, P.A.

(57) ABSTRACT

A medical device that may include a main body and a plurality of hooks. The main body includes a length extending along an axis between first and second ends. The main body may be deformable such that the axis forms an arch shape corresponding to a shape of a mandibular jaw or a maxillary jaw. The main body may include a plurality of sections each having first and second edges defining a first width and a plurality of openings disposed between the first and second edges and extending through a thickness of the main body. The main body may include a plurality of recessed portions defining a second width disposed between adjacent ones of the sections. Each of the hooks may extend from a corresponding one of the sections.

23 Claims, 8 Drawing Sheets

Related U.S. Application Data (60) Provisional application No. 61/980,910, filed on Apr. 17, 2014.

(58) Field of Classification Search
CPC .......... A61B 17/8023; A61B 2017/681; A43C 11/1493; A43C 11/10; A61C 7/00; A61C 7/36; A61C 8/0096
USPC ..................................................... 433/18–19
See application file for complete search history.

(56) References Cited

U.S. PATENT DOCUMENTS

| | | | |
|---|---|---|---|
| 7,172,422 B1 | 2/2007 | Essiger | |
| 8,062,032 B2 | 11/2011 | Bulloch et al. | |
| 8,118,850 B2 | 2/2012 | Marcus | |
| 8,435,270 B2 | 5/2013 | Furrer et al. | |
| 8,992,582 B1* | 3/2015 | Knoepfle | A61B 17/8028 606/281 |
| 10,531,900 B2* | 1/2020 | Ghobadi | A61B 17/8023 |
| 11,331,129 B2 | 5/2022 | Ghobadi et al. | |
| 2005/0038438 A1 | 2/2005 | Anderson et al. | |
| 2005/0192578 A1* | 9/2005 | Horst | A61B 17/8052 606/915 |
| 2007/0134623 A1* | 6/2007 | Essiger | A61F 2/2846 433/173 |
| 2007/0259306 A1 | 11/2007 | Raines et al. | |
| 2009/0170050 A1 | 7/2009 | Marcus | |
| 2011/0015681 A1* | 1/2011 | Elsbury | A61B 17/7059 606/281 |
| 2011/0022173 A1 | 1/2011 | Melkent et al. | |
| 2011/0152946 A1* | 6/2011 | Frigg | A61F 5/05891 606/300 |
| 2011/0152951 A1* | 6/2011 | Baker | A61C 7/00 606/328 |
| 2011/0269100 A1 | 11/2011 | Furrer et al. | |
| 2012/0010617 A1* | 1/2012 | Ramos Maza | A61B 17/8861 606/281 |
| 2012/0029576 A1* | 2/2012 | Cunliffe | A61B 17/8085 606/289 |
| 2012/0214120 A1 | 8/2012 | Marcus | |
| 2013/0052605 A1 | 2/2013 | Ahn | |
| 2013/0226247 A1* | 8/2013 | Furrer | A61B 17/8071 606/280 |
| 2013/0345813 A1* | 12/2013 | Frank | A61B 17/8023 623/17.16 |
| 2015/0073486 A1 | 3/2015 | Marotta et al. | |
| 2015/0297272 A1 | 10/2015 | Ghobadi et al. | |
| 2016/0008042 A1* | 1/2016 | Woodburn, Sr. | A61B 17/6433 606/328 |
| 2020/0222095 A1 | 7/2020 | Ghobadi et al. | |

OTHER PUBLICATIONS

"U.S. Appl. No. 14/530,902, Corrected Notice of Allowability dated Nov. 15, 2019", 5 pgs.
"U.S. Appl. No. 14/530,902, Examiner Interview Summary dated Jul. 31, 2019", 3 pgs.
"U.S. Appl. No. 14/530,902, Final Office Action dated Sep. 14, 2017", 33 pgs.
"U.S. Appl. No. 14/530,902, Final Office Action dated Oct. 22, 2018", 51 pgs.
"U.S. Appl. No. 14/530,902, Non Final Office Action dated Apr. 27, 2017", 35 pgs.
"U.S. Appl. No. 14/530,902, Non Final Office Action dated May 15, 2018", 49 pgs.
"U.S. Appl. No. 14/530,902, Non Final Office Action dated Jun. 21, 2019", 14 pgs.
"U.S. Appl. No. 14/530,902, Notice of Allowance dated Sep. 12, 2019", 6 pgs.
"U.S. Appl. No. 14/530,902, Response filed Jan. 22, 2019 to Final Office Action dated Oct. 22, 2018", 13 pgs.
"U.S. Appl. No. 14/530,902, Response filed Jul. 27, 2017 to Non Final Office Action dated Apr. 27, 2017", 11 pgs.
"U.S. Appl. No. 14/530,902, Response filed Aug. 13, 2019 to Non Final Office action dated Jun. 21, 2019", 10 pgs.
"U.S. Appl. No. 14/530,902, Response filed Aug. 15, 2018 to Non Final Office Action dated May 15, 2018", 13 pgs.
"U.S. Appl. No. 14/530,902, Response filed Nov. 14, 2017 to Final Office Action dated Sep. 14, 2017", 12 pgs.
U.S. Appl. No. 16/837,693, filed Apr. 1, 2020, Contourable Plate.
"U.S. Appl. No. 16/837,693, Advisory Action dated May 14, 2021", 4 pgs.
"U.S. Appl. No. 16/837,693, Final Office Action dated Jan. 8, 2021", 23 pgs.
"U.S. Appl. No. 16/837,693, Non Final Office Action dated Jul. 12, 2021", 16 pgs.
"U.S. Appl. No. 16/837,693, Non Final Office Action dated Sep. 25, 2020", 22 pgs.
"U.S. Appl. No. 16/837,693, Notice of Allowance dated Jan. 20, 2022", 5 pgs.
"U.S. Appl. No. 16/837,693, Response filed May 10, 2021 to Final Office Action dated Jan. 8, 2021", 14 pgs.
"U.S. Appl. No. 16/837,693, Response filed Jun. 26, 2020 to Restriction Requirement dated May 8, 2020", 9 pgs.
"U.S. Appl. No. 16/837,693, Response filed Dec. 10, 2021 to Non Final Office Action dated Jul. 12, 2021", 10 pgs.
"U.S. Appl. No. 16/837,693, Response filed Dec. 28, 2020 to Non Final Office Action dated Sep. 25, 2020", 13 pgs.
"U.S. Appl. No. 16/837,693, Restriction Requirement dated May 8, 2020", 6 pgs.

\* cited by examiner

CONTOURABLE PLATE

CROSS-REFERENCE TO RELATED APPLICATIONS

This application claims the benefit of U.S. Provisional Application No. 61/980,910, filed on Apr. 17, 2014. The entire disclosure of the above application is incorporated herein by reference.

FIELD

The present disclosure relates to a contourable plate for restricting movement of a patient's maxilla and mandible.

BACKGROUND

This section provides background information related to the present disclosure and is not necessarily prior art.

In certain circumstances, it may be desirable to stabilize and restrict relative movement between a patient's maxilla and mandible to promote bone healing following an injury to the patient's jaw, a surgical reconstruction, and/or a surgical alteration of the patient's jaw. Wire has been used in combination with various devices to retain the maxilla and mandible in a desired position. It may be desirable to provide a device and method for restricting the maxilla and mandible that reduces installation time relative to prior art devices and methods in a safe and effective manner.

SUMMARY

This section provides a general summary of the disclosure, and is not a comprehensive disclosure of its full scope or all of its features.

In one form, the present disclosure provides a medical device that may include a main body and a plurality of hooks. The main body includes a length extending along an axis between first and second ends. The main body may be deformable such that the axis forms an arch shape corresponding to a shape of a mandibular jaw or a maxillary jaw. The main body may include a plurality of sections each having first and second edges defining a first width and a plurality of openings disposed between the first and second edges and extending through a thickness of the main body. The main body may include a plurality of recessed portions defining a second width disposed between adjacent ones of the sections. Each of the hooks may extend from a corresponding one of the sections.

In some embodiments, each of the openings includes a chamfered surface extending only partially around a periphery of the opening.

In some embodiments, the hooks extend away from the axis.

In some embodiments, each of the hooks include a stem portion, a hooked lip and an elongated leg extending between the stem portion and the hooked lip.

In some embodiments, the stem portion of each hook is disposed at an angle relative to a corresponding section and a corresponding leg.

In some embodiments, the medical device includes a plurality of threaded fasteners configured to be driven through the openings.

In some embodiments, a thickness of the main body is less than or equal to a pitch of threads of the fasteners.

In some embodiments, the medical device includes a wire adapted to engage at least one of the hooks.

In some embodiments, each of the sections include a raised boss at least partially surrounding a corresponding one of the openings. The raised boss may have a thickness that is greater than a thickness of the recessed portions.

In another form, the present disclosure provides an intermaxillary fixation assembly that may include first and second contourable plates, a plurality of threaded fasteners, and at least one wire. The first and second contourable plates each have a main body and a plurality of hooks. The main body has a length extending along an axis between first and second ends. The main body may be deformable such that the axis forms an arch shape corresponding to a shape of a mandibular jaw or a maxillary jaw. The main body may include a plurality of sections each having first and second edges defining a first width and a plurality of openings disposed between the first and second edges and extending through a thickness of the main body. The main body may include a plurality of recessed portions defining a second width disposed between adjacent ones of the sections. Each of the hooks may extend from a corresponding one of the sections. The plurality of threaded fasteners may be adapted to threadably engage the openings and secure the first and second plates to a patient's maxilla and mandible, respectively. The at least one wire may be adapted to be attached to at least one hook of the first plate and at least one hook of the second plate.

In some embodiments, each of the openings include a chamfered surface extending only partially around a periphery of the opening.

In some embodiments, each of the hooks include a stem portion, a hooked lip and an elongated leg extending between the stem portion and the hooked lip. The stem portion of each hook may be disposed at an angle relative to a corresponding leg and a main body of a corresponding one of the first and second plates.

In another form, the present disclosure provides a method of restricting movement of a mandible relative to a maxilla that may include using first and second plates each having a plurality of openings formed therein and a plurality of hooks extending therefrom, each of the first and second plates having a plurality of recesses each disposed between a corresponding pair of adjacent openings. A user may bend the first plate at the recesses of the first plate into a first shape corresponding to a shape of the maxilla. The user may bend the second plate at the recesses of the second plate into a second shape corresponding to a shape of the mandible. The user may insert fasteners through the openings and drive the fasteners into the mandible or the maxilla.

In some embodiments, the user connects one of the hooks of the first plate to one of the hooks of the second plate.

In some embodiments, connecting one of the hooks of the first plate to one of the hooks of the second plate includes wrapping wire around distal ends of the hooks.

In some embodiments, the user positions the first and second plates such that tips of the hooks are vertically aligned with teeth extending from at least one of the maxilla and mandible.

In some embodiments, the user adjusts a length of at least one of the first and second plates. In some embodiments, adjusting a length of at least one of the first and second plates includes cutting at least one of the first and second plates at one of the recesses.

In some embodiments, the fasteners are locked relative to the first and second plates by engaging a thread of each of the fasteners with a chamfered surface of each of the openings. In some embodiments, the chamfered surface extends around only a portion of a periphery of the openings.

In another form, the present disclosure provides a medical device that may include an elongated, contourable bar having a plurality of hooks and a plurality of mounting tabs. Each of the hooks may include a stem that extends from the bar in a first direction. Each of the mounting tabs may extend from the bar in a second direction opposite the first direction and may include a pair of elongated apertures separated from each other by a support strut. Each of the mounting tabs may be spaced apart from each other.

In some embodiments, directly adjacent mounting tabs cooperate to form a U-shaped space therebetween.

In some embodiments, the bar is bendable from a pre-deployment configuration to a deployment configuration.

In some embodiments, in the pre-deployment configuration, the mounting tabs and the bar cooperate to define a flat plane and the bar defines a continuous curve about a first axis that extends perpendicular to the flat plane.

In some embodiments, in the deployment configuration, at least a portion of the bar is curved about a second axis perpendicular to the first axis.

In some embodiments, in the deployment configuration, the bar is shaped to correspond to a shape of a mandible or a maxilla.

In some embodiments, each of the elongated apertures includes a chamfered surface extending around a periphery thereof.

In some embodiments, the medical device includes a plurality of fasteners configured to be received in the elongated apertures.

In some embodiments, each of the fasteners includes a head and a shaft having a first threaded portion and a second threaded portion. The first threaded portion may include threads with a smaller diameter than threads of the second threaded portion. The threads of the second threaded portion may have a larger lead than the threads of the first threaded portion.

In some embodiments, each of the fasteners includes an annular locking groove disposed between the head and the second threaded portion. The second threaded portion may be disposed between the head and the first threaded portion.

In some embodiments, each of the elongated apertures includes a chamfered surface extending around a periphery thereof. An innermost peripheral edge of each elongated aperture may be configured to be received in the locking groove.

In another form, the present disclosure provides an intermaxillary fixation assembly including an elongated, contourable bar and a plurality of fasteners. The elongated, contourable bar may have a plurality of hooks and a plurality of mounting tabs. Each of the mounting tabs may include at least one aperture. The plurality of fasteners may be configured to be received in the apertures. Each of the fasteners may include a head and a shaft having a first threaded portion and a second threaded portion. The first threaded portion may have threads with a smaller lead than threads of the second threaded portion.

In some embodiments, each of the fasteners includes an annular locking groove disposed between the head and the second threaded portion. The second threaded portion may be disposed between the head and the first threaded portion.

In some embodiments, the threads of the first threaded portion may have a smaller diameter than the threads of the second threaded portion.

In some embodiments, each of the apertures includes a chamfered surface extending around a periphery thereof. An innermost peripheral edge of each aperture may be configured to be received in the locking groove.

In some embodiments, the mounting tabs include a pair of elongated apertures separated from each other by a support strut. Each of the mounting tabs may be spaced apart from each other.

In some embodiments, each of the hooks includes a stem that extends from the bar in a first direction. Each of the mounting tabs may extend from the bar in a second direction opposite the first direction.

In some embodiments, directly adjacent mounting tabs cooperate to form a U-shaped space therebetween.

In some embodiments, the bar is bendable from a pre-deployment configuration to a deployment configuration.

In some embodiments, in the pre-deployment configuration, the mounting tabs and the bar cooperate to define a flat plane and the bar defines a continuous curve about a first axis that extends perpendicular to the flat plane.

In some embodiments, in the deployment configuration, at least a portion of the bar is curved about a second axis perpendicular to the first axis.

In some embodiments, in the deployment configuration, the bar is shaped to correspond to a shape of a mandible or a maxilla.

In some embodiments, the intermaxillary fixation assembly of includes at least one wire and another elongated, contourable bar having a plurality of openings and a plurality of hooks. The at least one wire may engage at least one of the hooks of each of the bars.

In another form, the present disclosure provides a method of restricting movement of a mandible relative to a maxilla. The method may include using a first bar and a second bar each having a plurality of openings and a plurality of hooks; bending the first bar into a first shape corresponding to a shape of the maxilla; bending the second bar into a second shape corresponding to a shape of the mandible; inserting fasteners through the openings, the fasteners having a first threaded portion and a second threaded portion, the first threaded portion having threads with a smaller diameter than threads of the second threaded portion; threadably driving the first threaded portion one of the fasteners into the mandible or the maxilla; engaging the second threaded portion of the one of the fasteners with a periphery of a corresponding opening; and rotating the one of the fasteners relative to the bars and relative to the mandible or maxilla such that the one of the fasteners is threadably advanced into the mandible or maxilla while simultaneously threadably moving at least a portion of one of the first and second bars toward a head of the one of the fasteners and away from gingival tissue through which the fasteners extend.

In some embodiments, the method includes connecting one of the hooks of the first bar to one of the hooks of the second bar.

In some embodiments, connecting one of the hooks of the first bar to one of the hooks of the second bar includes wrapping wire around distal ends of the hooks.

In some embodiments, the method includes positioning the first and second bars such that tips of the hooks are vertically aligned with teeth extending from at least one of the maxilla and mandible.

In some embodiments, the method includes locking the fasteners relative to the first and second bars by engaging an annular locking groove of the fasteners with chamfered surfaces of the openings.

In some embodiments, engagement between the locking groove and the chamfered surfaces is an interference fit.

In some embodiments, bending the first bar includes bending the first bar from a pre-deployment shape to the shape corresponding to the maxilla. In the pre-deployment shape, the bar and mounting tabs through which the openings extend may cooperate to define a flat plane and the bar may define a continuous curve about an axis that extends perpendicular to the flat plane.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
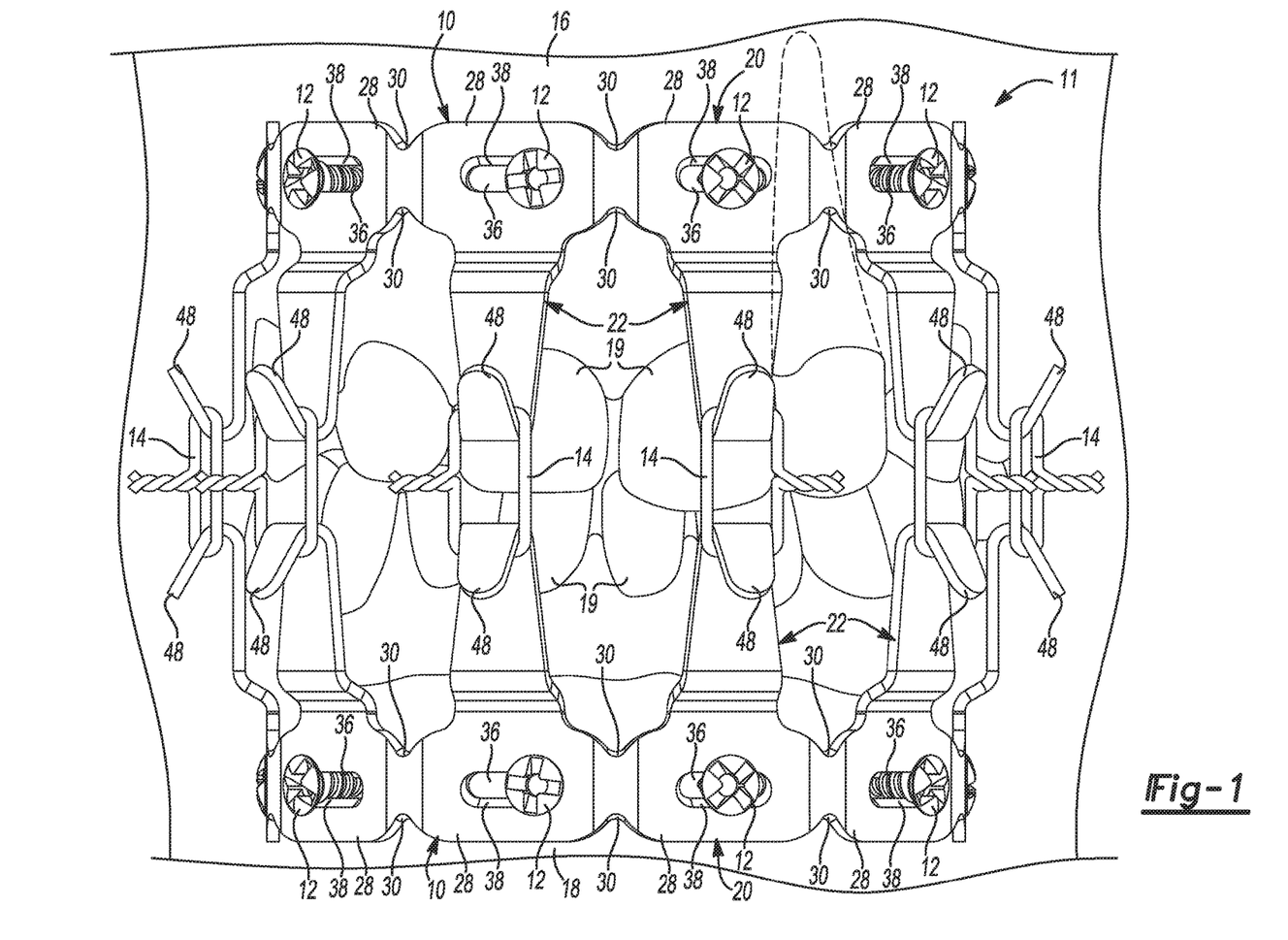
FIG. 1 is a perspective view of a pair of contourable plates attached to a patient's maxilla and mandible according to the principles of the present disclosure.

With reference to FIG. 1, an intermaxillary fixation assembly 11 is provided that may include a pair of contourable plates or arch bars 10, a plurality of threaded fasteners 12 and one or more rubber bands or wires 14. The fasteners 12 secure the plates 10 to a respective one of a patient's maxilla 16 and mandible 18. Thereafter, a surgeon may use the one or more wires 14 to secure the two plates 10 to each other, thereby restricting relative movement between the patient's maxilla and mandible. In some embodiments, the plates 10 are similar or identical to each other. Each of the plates 10 may be bent or contoured by the surgeon (or another medical professional) to correspond to the shapes of an individual patient's maxilla and mandible, respectively.

Figure 2:
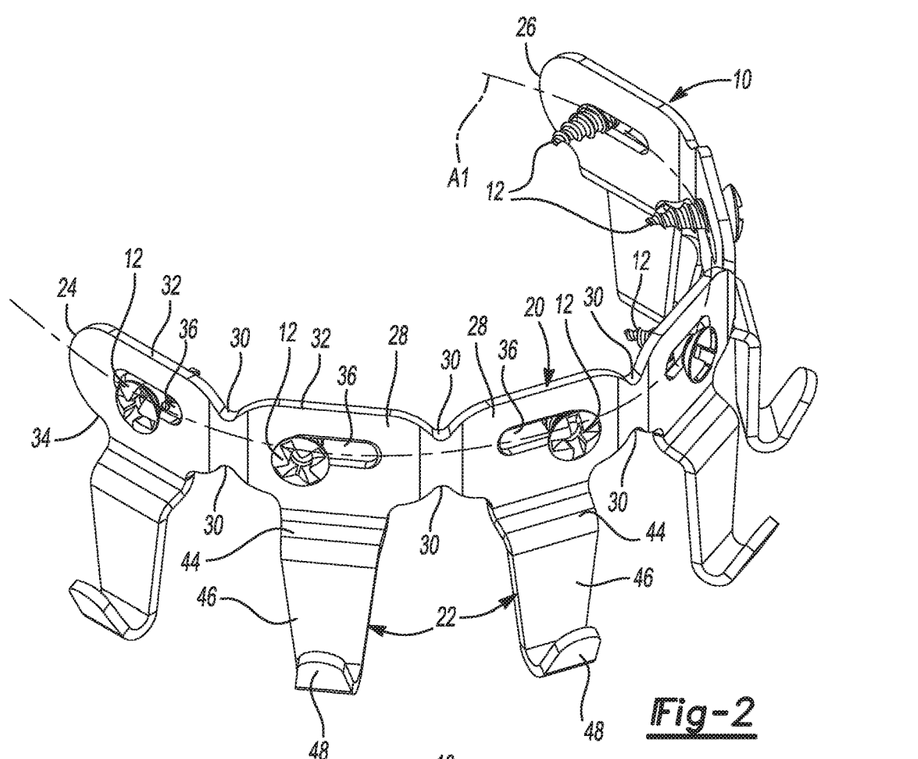
FIG. 2 is a perspective view of one of the contourable plates of FIG. 1 in a contoured condition.
Figure 3:
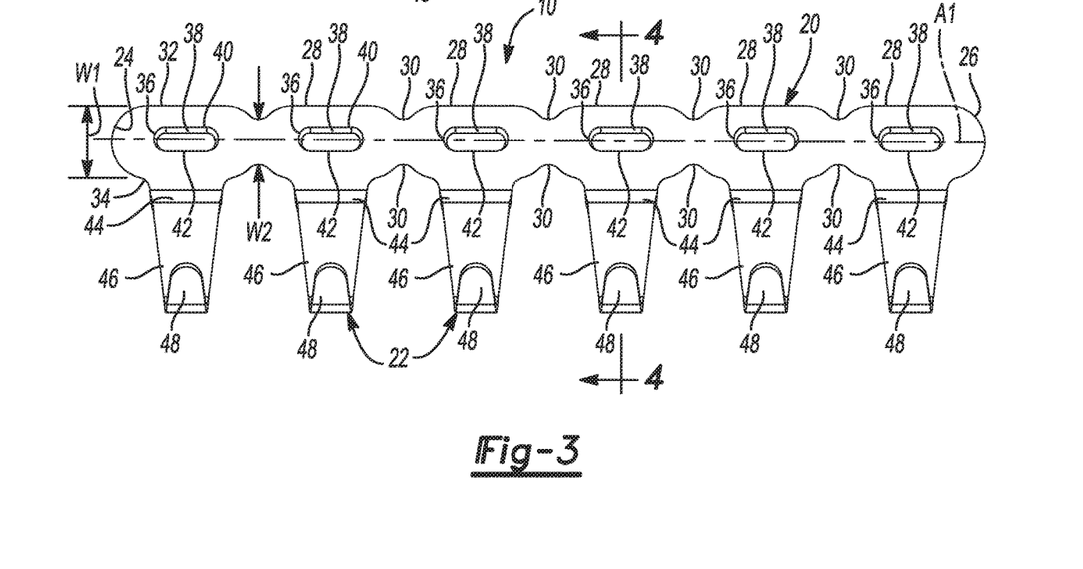
FIG. 3 is a plan view of the contourable plate in a flat condition.

Referring now to FIGS. 1-4, each of the plates 10 may include an elongated main body 20 and a plurality of hooks 22 extending therefrom. An axis A1 (FIGS. 2 and 3) may extend through first and second ends 24, 26 of the main body 20. The main body 20 may include a plurality of sections 28 and a plurality of recesses 30. Each of the recesses 30 may be disposed between adjacent sections 28. Each of the sections 28 may include first and second edges 32, 34 that define a first width W1 (FIG. 3) of the sections 28. The recesses 30 may have a second width W2 (FIG. 3) that is smaller than the first width W1. The recesses 30, having the smaller second width W2, facilitate bending of the main body 20 into a shape corresponding to a particular patient's maxilla or mandible, as shown in FIGS. 1 and 2. It will be appreciated that each section 28 may be bendable or contourable. That is, bending of the main body 20 may not be limited to bending only at the recesses 30. The recesses 30 may also facilitate cutting of the main body 20 into multiple pieces and/or trimming the main body 20 to a desired length.

Each of the sections 28 may include an opening or aperture 36 extending therethrough. As shown in FIGS. 1 and 2, the fasteners 12 extend through the apertures 36 and engage bone and/or other tissue. While the apertures 36 are shown in the figures as elongated slots that extend longitudinally along the axis A1, in other embodiments, the apertures 36 could be generally circular holes or the apertures 36 could be slots that are elongated in directions perpendicular to the axis A1. The elongated shape of the apertures 36 allows the surgeon freedom to locate the fasteners 12 in desired positions to avoid driving the fasteners 12 into major nerves, roots of teeth, or sensitive and/or damaged bone or tissue, for example.

In some embodiments, each aperture 36 may include a chamfered surface 38 (FIGS. 3 and 4) that extends only partially around a periphery of the aperture 36. In the particular configuration illustrated, a first elongated edge 40 of the aperture 36 includes the chamfered surface 38 while the second parallel edge 42 of the aperture 36 is not chamfered. The single chamfered surface 38 allows for engagement with the threads of the fasteners 12. In some embodiments, a thickness of the main body 20 may be less than or equal to a pitch of the threads of the fasteners 12. In some embodiments, the distance between the first and second edges 40, 42 may be between approximately a minor diameter of the threads of the fastener 12 and approximately 75% of the distance between the minor and major diameters of the threads of the fastener 12. The fasteners 12 may threadably engage the apertures 36 and may be threadably advanced through the apertures 36. The fasteners 12 may be cam-locked in the apertures 36 when a thread runout of the fastener 12 (i.e., an end of the thread of the fastener 12 closest to the head of the fastener 12) cam-locks against the edges 40, 42 of the aperture 36.

Figures 4, 5:
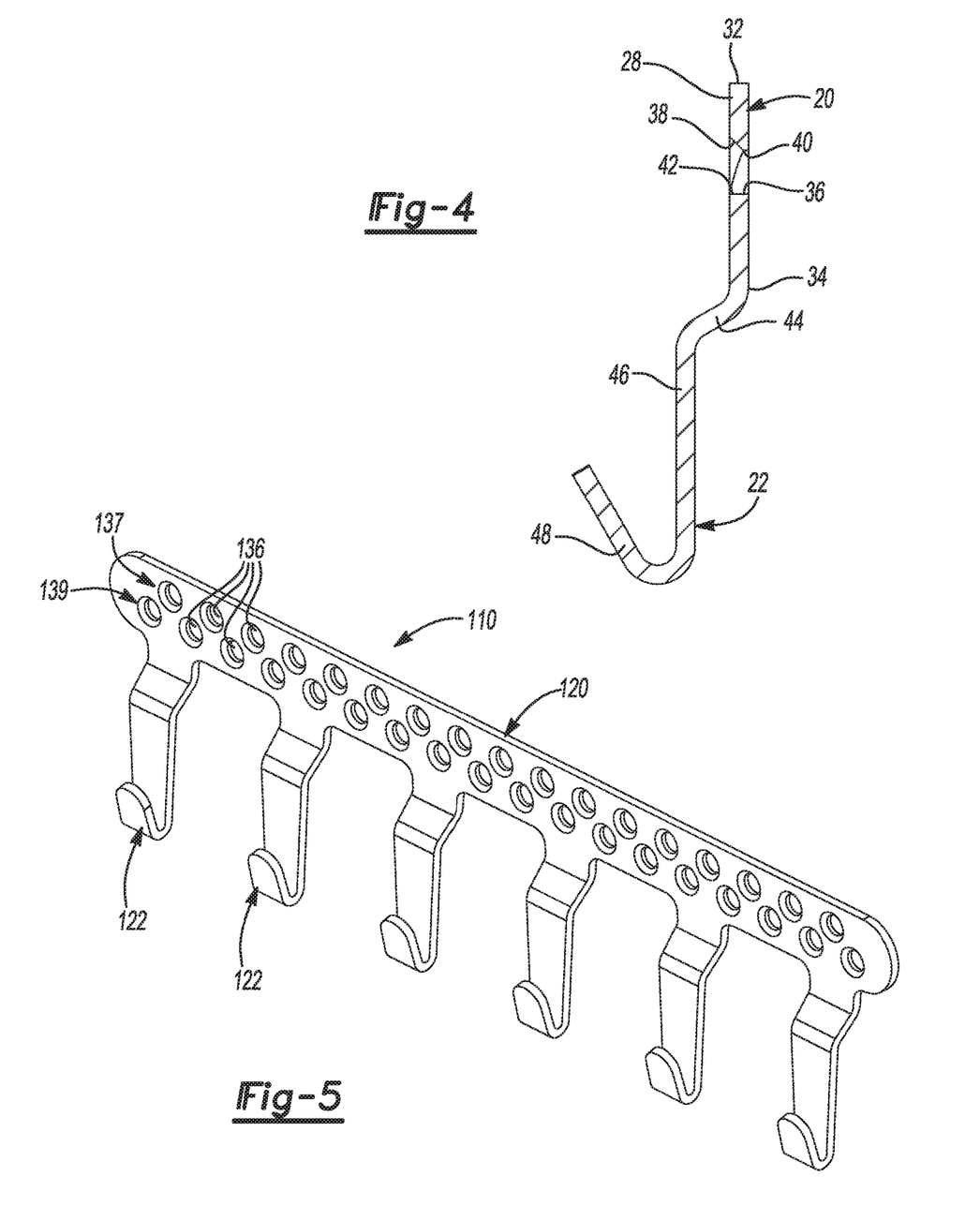
FIG. 4 is a cross-sectional view of the contourable plate taken along line 4-4 of FIG. 3.
FIG. 5 is a perspective view of another contourable plate in a flat condition according to the principles of the present disclosure.

Each of the plurality of hooks 22 may extend from the second edge 34 of a corresponding one of the sections 28 of the main body 20. The hooks 22 may extend away from the axis A1. Each of the hooks 22 may include a stem portion 44, an elongated leg 46 and a hooked lip 48. As shown in FIG. 4, the stem portion 44 may be bent to extend at an angle relative to the main body 20. For example, in some embodiments, the stem portion 44 may be bent at approximately a sixty degree angle relative to the main body 20. In some embodiments, the angle of the stem portion 44 relative to the main body 20 may be chosen to accommodate the shape of the patient's maxilla 16 or mandible 18 and the patient's teeth 19 so that the main body 20 may contact the patient's mandible or maxilla and the leg 46 of the hooks 22 may contact or nearly contact the patient's teeth 19.

With continued reference to FIGS. 1-4, a method of restricting movement between the patient's maxilla 16 and mandible 18 will be described. As described above and shown in FIG. 1, a surgeon may attach one of the contourable plates 10 to each of the patient's maxilla 16 and mandible 18 with the fasteners 12 and secure the two plates 10 to each other with metallic or polymeric wire 14, thereby restricting relative movement between the patient's maxilla 16 and mandible 18.

Before attaching the plates 10 to the patient's maxilla 16 and mandible 18, the surgeon may trim the length of the plates 10 and/or bend the plates 10 to generally match the shape and contours of the particular patient's maxilla 16 and mandible 18 (as shown in FIGS. 1 and 2). As described above, the trimming and bending of the plates 10 may occur at one or more of the recesses 30 of the main body 20 and/or anywhere along one or more of the sections 28 of the main body 20.

Next, the surgeon may position one of the plates 10 inside of the patient's mouth so that the main body 20 of the plate 10 is placed in a desired location against one of the patient's maxilla 16 and mandible 18 (e.g., in contact with the patient's gum tissue covering the maxilla 16 or mandible 18 generally adjacent the patient's teeth 19). Then, the surgeon may drive one or more of the fasteners 12 through one or more of the apertures 36 and into the patient's tissue and bone. The surgeon may repeat this process to attach a second one of the plates 10 into the other of the patient's maxilla 16 or mandible 18. As described above, the surgeon may select locations in the patient's bone and tissue into which the fasteners 12 are driven to minimize or reduce damage to the patient's bone, tissue and/or nerves and/or to minimize or reduce pain that the patient will experience as a result of the installation of the plates 10.

With the plates 10 secured to the patient's maxilla 16 and mandible 18, the surgeon may loop strands of wire 14 around the lips 48 of the hooks 22 of the plates 10 and twist and/or tie the ends of the wires 14 to each other to secure the plates 10 to relative to each other, and thereby restrict relative motion between the maxilla 16 and mandible 18. While each wire 14 is shown looped around one of the hooks 22 of each plate 10, it will be appreciated that the wire 14 can be laced, tied or wrapped around any number of hooks 22 of each plate 10 in any desired manner. Instead of or in addition to the wires 14, the surgeon may choose to use rubber bands and/or any other suitable band, tie or clip, for example, to secure the plates 10 to each other.

Attaching the plates 10 to the patient's maxilla 16 and mandible 18 with the fasteners 12 and attaching the wire 14 to the extended hooks 22 allows the surgeon to quickly and safely complete installation of the assembly 11. Wrapping the wire 14 around the hooks 22 allows the wire 14 to be attached without having the pass the wire 14 between teeth 19. The assembly 11 and method described above provides a safe and robust way of stabilizing the patient's jaw in a manner that is not dependent upon the positioning or structural integrity of the patient's teeth and is not affected by a lack of the patient's teeth.

With reference to FIG. 5, another contourable plate 110 is provided that may be generally similar to the plates 10 described above apart from any exceptions described below and/or shown in the figures. Two of the plates 110 can be used in combination with the fasteners 12 and wire 14 in substantially the same manner described above to restrict relative movement between the patient's maxilla 16 and mandible 18.

The plate 110 may include a main body 120 and a plurality of hooks 122 extending therefrom. The hooks 122 may be similar or identical to the hooks 22 described above. The main body 120 may include a plurality of apertures 136 arranged in first and second rows 137, 139. The first and second rows 137, 139 may extend generally parallel to each other and may be vertically (relative to the view shown in FIG. 5) spaced from each other. Each aperture 136 in the first row 137 may be positioned horizontally (relative to the view shown in FIG. 5) between adjacent apertures 136 of the second row 139. In this manner, the surgeon may select desired ones of the apertures 136 through which to pass fasteners 12 to fasten the plate 110 to the patient's bone or tissue. As described above, the surgeon may select the apertures 136 based on the positioning of the selected apertures 136 relative to locations of particular anatomical features such as major nerves and/or roots of teeth, for example.

Figures 6, 7:
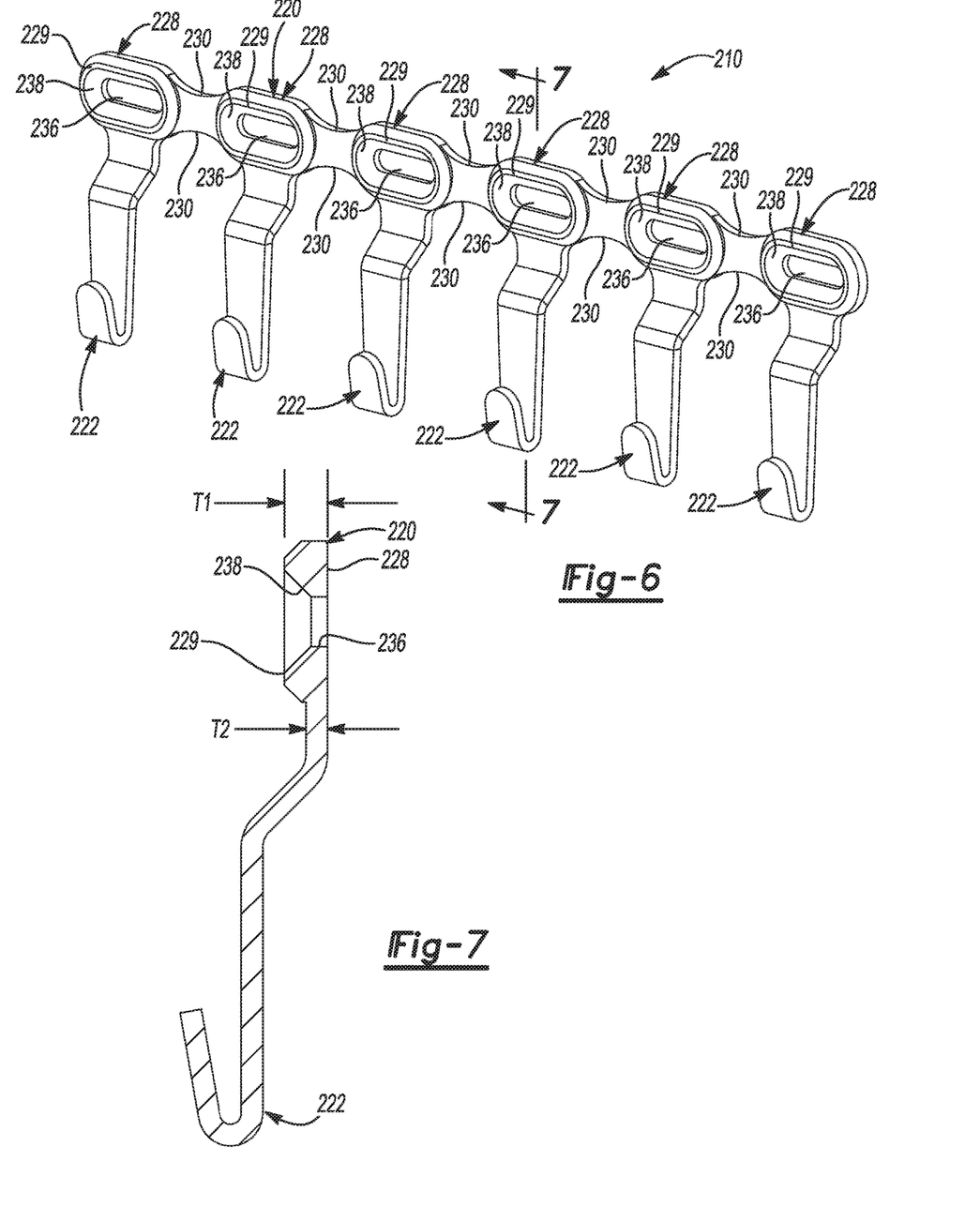
FIG. 6 is a perspective view of yet another contourable plate in a flat condition according to the principles of the present disclosure.
FIG. 7 is a cross-sectional view of the contourable plate of FIG. 6 taken along line 7-7 of FIG. 6.

With reference to FIGS. 6 and 7, another contourable plate 210 is provided that may be generally similar to the plates 10 described above apart from any exceptions described below and/or shown in the figures. Two of the plates 210 can be used in combination with the fasteners 12 and wire 14 in substantially the same manner described above to restrict relative movement between the patient's maxilla 16 and mandible 18.

The plate 210 may include a main body 220 and a plurality of hooks 222 extending therefrom. The hooks 222 may be similar or identical to the hooks 22 described above. The main body 220 may include a plurality of sections 228 and a plurality of recesses 230. Each of the recesses 230 may be disposed between adjacent sections 228. Like the recesses 30, the recesses 230 may have a smaller width than the sections 228 to facilitate bending and/or trimming of the plate 210 to fit the plate 210 to the anatomy of a particular patient. Each of the sections 228 may include an aperture 236. The apertures 236 may be elongated slots or circular holes, for example. Each of the sections 228 may include a raised boss 229 that extends around the aperture 236. The bosses 229 may include a first thickness T1 that is greater than a second thickness T2 of the hooks 222 and recesses 230. A chamfer 238 may be formed around some or all of each of the apertures 236. The increased thickness of the bosses 229 may increase the amount of engagement between the fasteners 12 and the plate 210, thereby increasing the ability to lock the fasteners 12 in the apertures 236.

Figure 8:
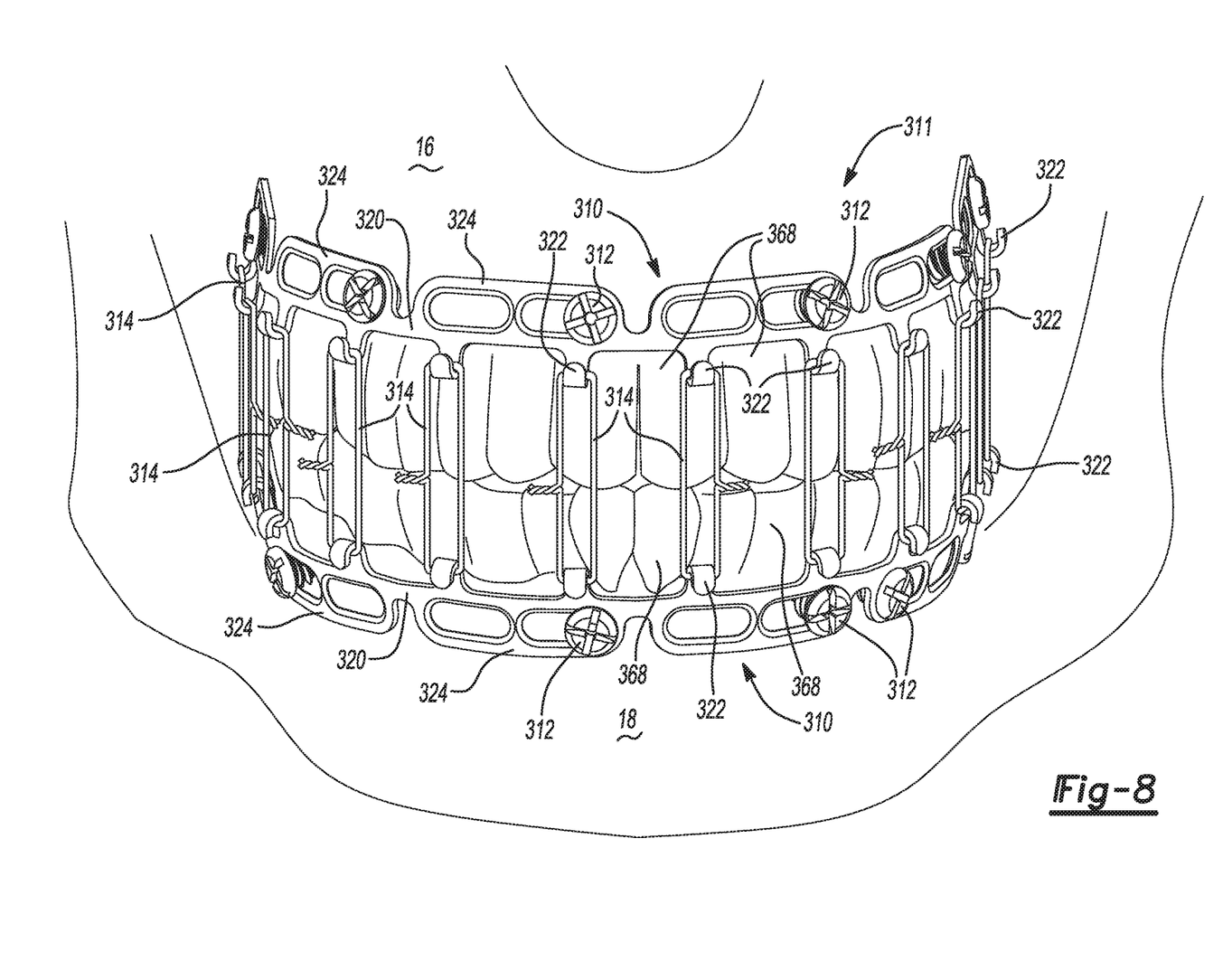
FIG. 8 is a perspective view of an intermaxillary fixation assembly include another pair of contourable plates attached to a patient's maxilla and mandible according to the principles of the present disclosure.

With reference to FIGS. 8-13, another intermaxillary fixation assembly 311 is provided that may include a pair of contourable plates or arch bars 310, a plurality of threaded fasteners 312 and one or more bands or wires 314 (FIG. 8). Some of the fasteners 312 may fix one of the arch bars 310 to a patient's maxilla 16, and some of the fasteners 312 may fix the other one of the arch bars 310 to the patient's mandible 18. The wires 314 may secure the two arch bars 310 to each other, thereby restricting relative movement between the patient's maxilla 16 and mandible 18. In some embodiments, the arch bars 310 are similar or identical to each other. Each of the arch bars 310 may be bent or contoured by the surgeon (or another medical professional) to correspond to the shapes of an individual patient's maxilla and mandible, respectively.

Figure 11:
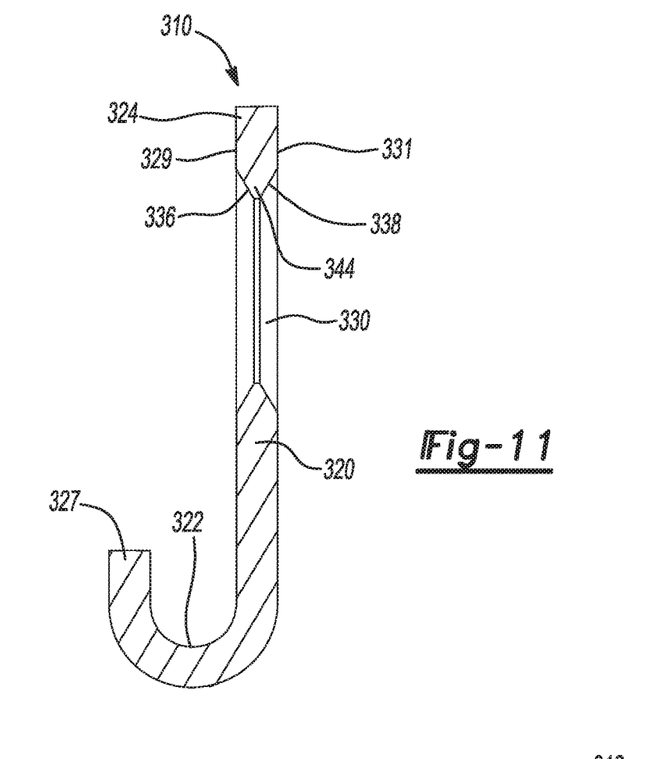
FIG. 11 is a cross-sectional view of one of the contourable plates of FIG. 8.

Each of the arch bars 310 include an elongated, contourable bar 320 having a plurality of hooks 322 and a plurality of mounting tabs 324. A stem 325 of each of the hooks 322 may extend from a first edge 326 of the bar 320 in a first direction. As shown in FIG. 11, the hooks 322 may include generally U-shaped or J-shaped cross sections such that free ends 327 of the hooks 322 are spaced apart from an anterior side 329 of the arch bar 310.

The mounting tabs 324 and the bar 320 cooperate to form a main body of the arch bar 310. The mounting tabs 324 may extend from a second edge 328 (opposite the first edge 326) (FIG. 10) of the bar 320 in a second direction opposite the first direction. Each mounting tab 324 may include one or more apertures 330 extending therethrough. In the configuration depicted in FIGS. 8-13, each mounting tab 324 includes a pair of elongated slots or apertures 330. Each mounting tab 324 includes a support strut 332 separating adjacent apertures 330. The mounting tab 324 may be spaced apart from each other such that directly adjacent mounting tabs cooperate to form a generally U-shaped space or recess 334 (FIG. 10) therebetween. The mounting tabs 324 and the bar 320 cooperate to form a first width of the main body of the arch bar 310, and the first and second edges 326, 328 cooperate to form a second width of the main body that is smaller than the first width.

First and second chamfers 336, 338 surround a periphery of each of the apertures 330. The first chamfer 336 may be formed on the anterior side 329 of the arch bar 310, and the second chamfer 338 may be formed on a posterior side 331 of the arch bar 310. The first and second chamfers 336, 338 of each aperture 330 cooperate to define a tapered rim 344 (FIG. 11) defining the periphery of the aperture 330.

Figure 9:
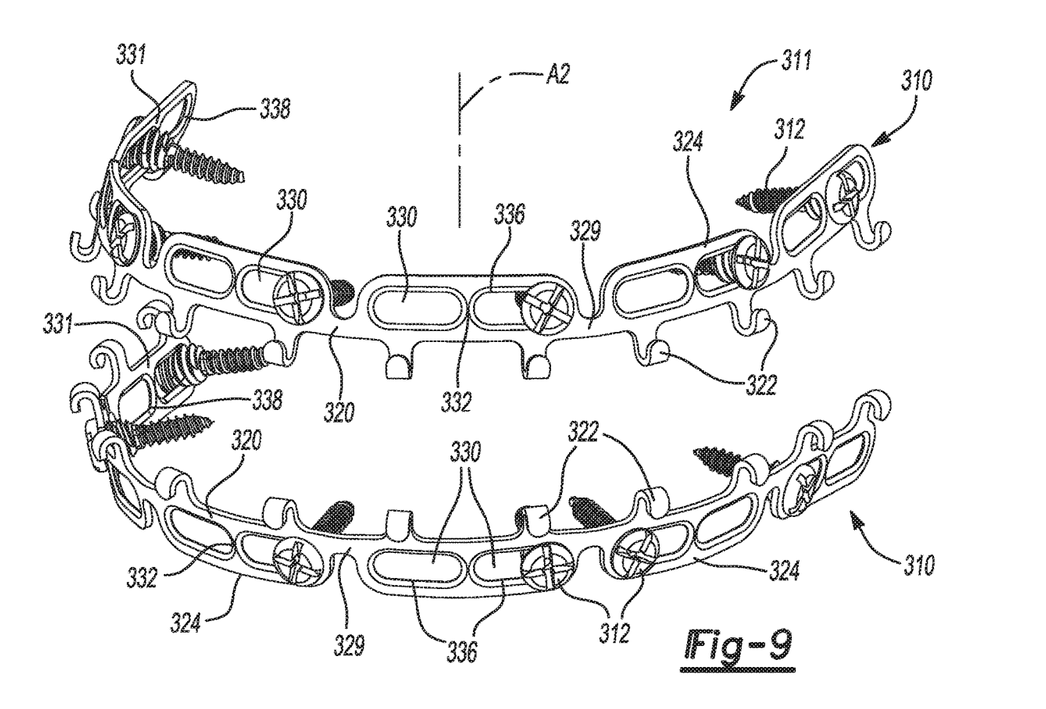
FIG. 9 is a perspective view of the contourable plates of FIG. 8 in a deployment configuration.

The arch bars 310 are bendable and plastically deformable from a pre-deployment configuration (shown in FIG. 10) to a deployment configuration (shown in FIGS. 8 and 9). In the pre-deployment configuration, the bar 320 and the mounting tabs 324 define a flat plane (i.e., the bar 320 and all of the mounting tabs 324 lie on the same flat plane), and the bar 320 defines a continuous curve about a first axis A1 (shown extending into the page in FIG. 10) that extends perpendicular to the flat plane. It should be appreciated that the positioning of first axis A1 in FIG. 10 relative to the bar 320 is not to scale relative to the radius of the curvature of the bar 320.

A surgeon or other medical professional may bend the arch bars 310 to the deployment configurations. The shapes of the arch bars 310 in the deployment configurations may correspond to the shapes of the maxilla 16 and mandible 18 of a particular patient to which the particular arch bars 310 will be fixed. In the deployment configuration, the opposing ends of each arch bar 310 may be bent toward each other. That is, some of or the entire arch bar 310 may be bent about one or more second axes A2 that may be perpendicular to the first axis A1.

Figure 12:
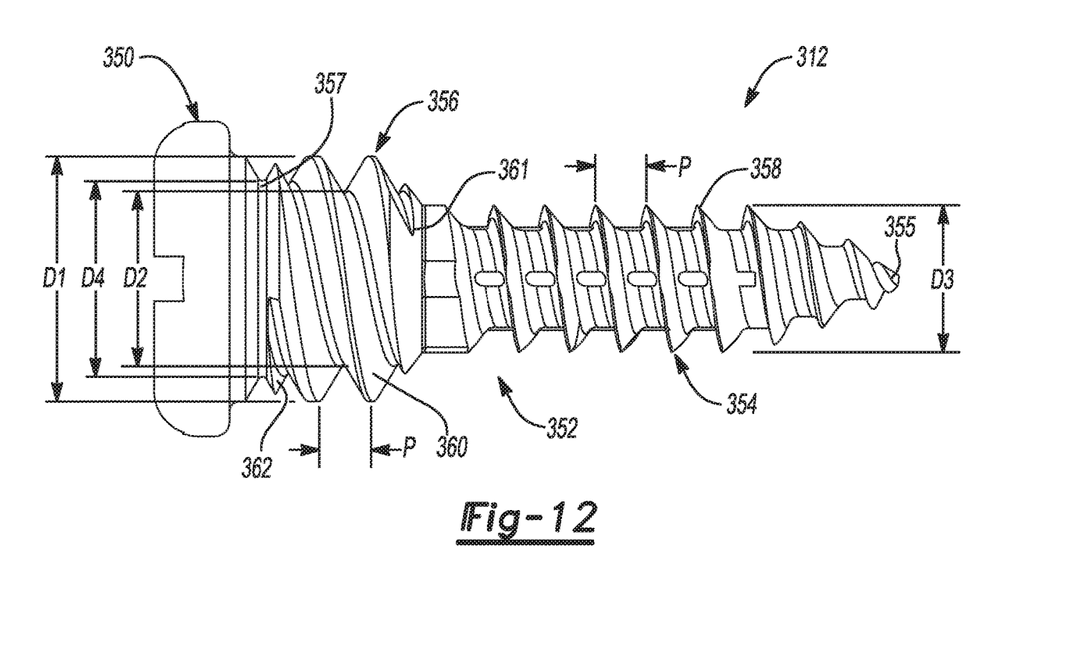
FIG. 12 is a side view of a fastener of the intermaxillary fixation assembly of FIG. 8.
Figure 13:
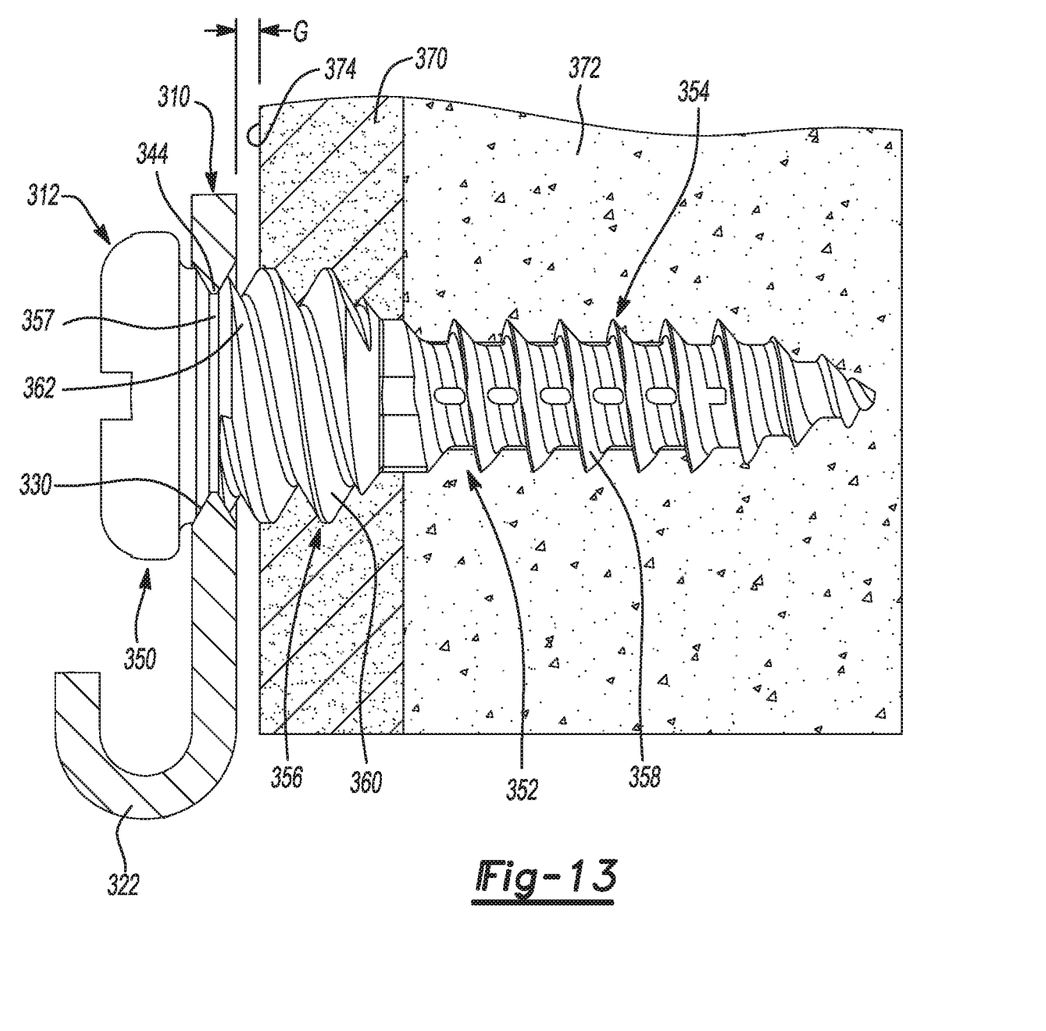
FIG. 13 is a cross-sectional view of the fastener engaging the contourable plate and a patient's tissue.

As shown in FIGS. 12 and 13, the fasteners 312 may include a head 350 and a shaft 352. The shaft 352 may include a first threaded portion 354, a second threaded portion 356, and an annular locking groove 357. The first threaded portion 354 may include a tip 355 of the fastener 312 and a first set of threads 358. The first set of threads 358 could be bone-screw threads, for example.

The second threaded portion 356 may be disposed between the head 350 and the first threaded portion 354 and may include a second set of threads 360 having a larger diameter than the first set of threads 358 (e.g., major and minor diameters D1, D2 of the second set of threads 360 may both be larger than the major diameter D3 of the first set of threads 358. The second set of threads 360 may have twice the lead as the first set of threads 358. That is, one full rotation of the fastener 312 relative to an object threadably engaged with the second set of threads 360 will result in double the relative linear axial movement between the fastener 312 and the object as compared to the length of the relative linear axial movement that would result if the object were threadably engaged with the first set of threads 358 for one full rotation of the fastener relative to the object. In some embodiments, the second set of threads 360 may have two starts 361 (i.e., two separate threads that are 180 degrees out of phase with each other) and the same (or nearly the same) pitch P (axial distance between adjacent threads) as the first set of threads 358, thereby giving the second set of threads 360 twice the lead as the first set of threads 358. In other embodiments, the second set of threads 360 could have a single start (one single continuous thread extending from one axial end of the second threaded portion 356 to the other axial end) and twice the pitch as the first set of threads 358, thereby giving the second set of threads 360 twice the lead as the first set of threads 358. In some embodiments, the lead of the second set of threads 360 could be more or less than twice the lead of the first set of threads 358.

The locking groove 357 may be an annular groove disposed between the head 350 and the second threaded portion 356. The minor diameter D4 of the locking groove 357 may be greater than the minor diameter D2 of the second set of threads 360 and less than the major diameter D1 of the second set of threads 360. The second set of threads 360 may include a tapered section 362 adjacent the locking groove 357 that provides a gradual, ramped transition from the minor diameter D2 of the second set of threads 360 to the minor diameter D4 of the locking groove 357. The minor diameter D4 of the locking groove 357 may be sized for a tight fit or an interference fit with the tapered rim 344 defining the periphery of the aperture 330 of the arch bar 310 when the rim 344 is received in the locking groove 357 (as shown in FIG. 13). Such a fit prevents the relative sliding between the fasteners 312 and the apertures 330 while still allowing the fasteners 312 to rotate within the apertures 330 if adjustments need to be made to the depth of the fasteners 312 relative to the patient's tissue while the rims 344 are received in the locking grooves 357.

With continued reference to FIGS. 8-13, a method of method of restricting movement between the patient's maxilla 16 and mandible 18 using the intermaxillary fixation assembly 311 will be described. As described above, the arch bars 310 are bendable from the pre-deployment configuration (FIG. 10) to the deployment configuration (FIGS. 8 and 9). That is, the surgeon or other medical professional may bend one of the arch bars 310 into a shape corresponding to the shape of the particular patient's maxilla 16. The surgeon or other medical professional may bend the other arch bar 310 into a shape corresponding to the shape of the particular patient's mandible 18.

Figure 10:
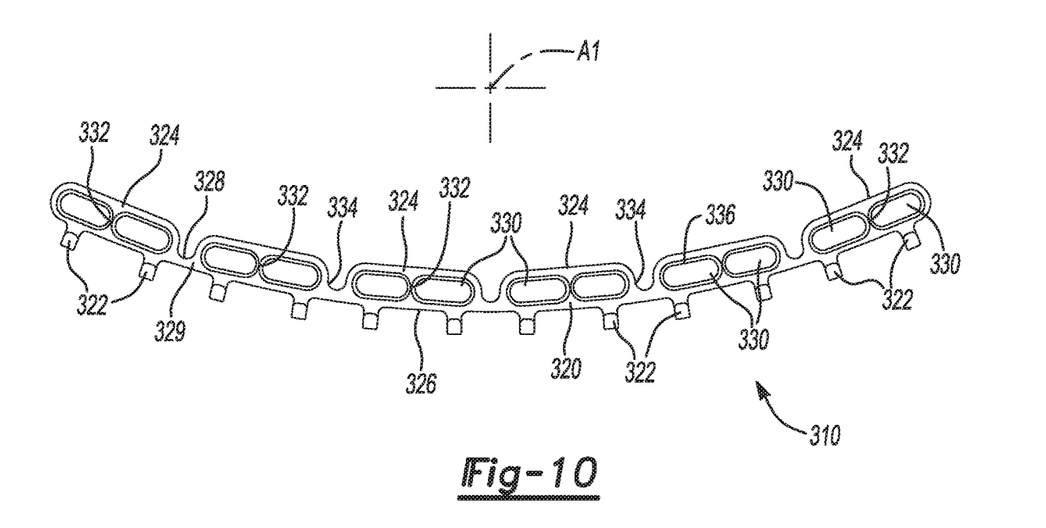
FIG. 10 is a perspective view of one of the contourable plates of FIG. 8 in a pre-deployment configuration.

The "in-plane contour" of the arch bar 310 in the pre-deployment configuration (i.e., the curve of the arch bar 310 about the first axis A1 shown in FIG. 10) may facilitate "out-of-plan" bending of the arch bar 310 into desired deployment configurations. That is, the in-plane contour may make it easier for the surgeon to bend the arch bar 310 in a manner that produces consistent localized bends without causing creasing or "tenting" of the arch bar 310. In this manner, the surgeon has more control over shaping of the arch bar 310 to suit shape of a given patient's maxilla or mandible.

With the arch bars 310 at least partially bent into the desired deployment configuration, the surgeon may position the arch bars 310 relative to the maxilla 16 and mandible 18 as desired and drive fasteners 312 through selected ones of the apertures 330 and into the patient's maxilla 16 or mandible 18 (as shown in FIGS. 8 and 13). As shown in FIG. 8, the arch bars 310 may be positioned near the patient's gum line so that the hooks 322 are vertically positioned generally in alignment with the patient's teeth 368.

The apertures 330 chosen for receiving the fasteners 312 and the particular location in each aperture chosen for receiving the fasteners 312 may be chosen based on the underlying anatomy of the patient. For example, the surgeon can chose certain apertures 330 and locations within the apertures 330 (i.e., positions along the lengths of the apertures 330) to avoid tooth roots, certain nerves, muscle and/or bone structures and/or target other bone or tissue structures that may be better suited for receiving the fasteners 312.

The surgeon may drive each fastener 312 into the patient's maxilla 16 or mandible 18 by first driving the first threaded portion 354 of the fastener 312 through gingival tissue 370 (FIG. 13) and into bone structure 372 (FIG. 13). As the first threaded portion 354 continues to be driven into the bone structure 372, the second threaded portion 356 will threadably engage the rim 344 of the aperture 330 of the arch bar 310. Because the second set of threads 360 of the second threaded portion 356 has twice the lead as the first set of threads 358 of the first threaded portion 354, threadably advancing the fastener 312 deeper into the bone structure 372 while the rim 344 is engaged with the second set of threads 360 will cause the arch bar 310 to move away from the tissue 370 and toward the head 350 of the fastener 312 until the rim 344 seats within the locking groove 357 of the fastener 312 (as shown in FIG. 13).

The interference fit or tight fit of the rim 344 in the locking groove 357 restricts or prevents the rim 344 from disengaging the locking groove 357 and restricts or prevents relative movement between the fastener 312 and the arch bar 310 along the elongated length of the aperture 330 while still allowing the fastener 312 to rotate relative to the arch bar 310. In this manner, the surgeon may adjust the depth of the fastener 312 into the patient's bone 372 to adjust a gap G between the arch bar 310 and the outer surface 374 of the tissue 370. The tapered section 362 of the second set of threads 360 provides a ramped transition from the minor diameter D2 of the second set of threads 360 to the minor diameter D4 of the locking groove 357 and may allow for the gradual expansion of the aperture 330 as the rim 344 approaches its seat in the locking groove 357. Furthermore, the tapered section 362 may reduce sensitivity to off-angle insertion of the fastener 312 into the tissue 370 and bone 372.

It will be appreciated that the gap G between the arch bar 310 and the outer surface 374 may vary at different locations along the length of the arch bar 310. That is, the surgeon could choose to vary the gap G at or more fasteners 312 by adjusting the depth of individual fasteners 312 in the bone structure 372. This allows the surgeon to make localized fine adjustments to the out-of-plane contour of the arch bar 310 without inducing anterior "tenting" of the arch bar 310. Furthermore, providing the gap G between the arch bar 310 and the gingival tissue 370 prevents compression of the tissue 370, thereby reducing or minimizing necrosis of the tissue 370. Because of the tendency of the second set of threads 360 of the fasteners 312 to move the arch bar 310 away from the tissue 370 and toward the head 350 of the fastener 312 (due to the larger lead of the second set of threads 360 relative to the first set of threads 358), the gap G can be created without having to insert a spacer tool between the arch bar 310 and the tissue 370 during installation of the intermaxillary fixation assembly 311.

The support strut 332 between adjacent apertures 330 on each mounting tab 324 reduces the variation in stiffness of the arch bar 310 along the length of the arch bar 310, while still allowing for a wide range of placement options for the fasteners 312. The support struts 332 also reduce or minimize an amount of the arch bar 310 that "hangs" posterior of the last fastener 312 securing the arch bar 310 to the bone 372 (i.e., the support struts 332 provide additional stiffness for ends of the arch bars 310). In this manner, undesirable flexing in the posterior aspects (distal ends) of the arch bars 310 is reduced.

Once the surgeon has inserted the desired number of fasteners 312 into the desired locations and the arch bars 310 are positioned as desired, the surgeon may tie or wrap one or more of the wires 314 around the hooks 322 of the arch bars 310 to restrict relative movement between the maxilla 16 and mandible 18. It will be appreciated that adjustments can be made to the fasteners 312 after attachment of the one or more wires 314 to the hooks 322 and/or additional fasteners 312 could be driven into the bone 372 after attachment of the one or more wires 314 to the hooks 322.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for stabilizing a maxilla or a mandible of a patient, the system comprising:
   a main body having a length extending along a longitudinal axis between first and second ends,
   the main body being deformable such that the longitudinal axis forms an arch shape corresponding to a shape of the maxilla or the mandible,
   the main body having a plurality of sections each having top and bottom edges defining a first width and a plurality of openings that are oblong and are disposed between the top and bottom edges of each section of the plurality of sections and extending through a thickness of the main body, wherein the plurality of openings are positioned side-by-side along an axis that is parallel to the longitudinal axis of the main body,
   the main body including a plurality of recessed portions defining a second width disposed between adjacent sections of the plurality of sections,
   each hook of the plurality of hooks extending from a corresponding section of the plurality of sections and away from the longitudinal axis, each hook of the plurality of hooks extending from the bottom edge of the corresponding section to a terminal hook edge, wherein the terminal hook edge is positioned below the plurality of openings,
   wherein each section of the plurality of sections includes a support strut positioned between the plurality of openings.

2. The system of claim 1, wherein the terminal hook edge of each hook of the plurality of hooks is positioned approximately below the bottom edge of each of the plurality of sections.

3. The system of claim 1, wherein each hook of the plurality of hooks is positioned longitudinally away from the plurality of recessed portions.

4. The system of claim 1, wherein each hook of the plurality of hooks includes a stem portion, a hooked lip and an elongated leg extending between the stem portion and the hooked lip wherein the stem portion of each hook of the plurality of hooks is disposed at an angle relative to a corresponding section and a corresponding leg.

5. The system of claim 1, further comprising a plurality of threaded fasteners configured to be driven through the plurality of openings, wherein a thickness of the main body is less than or equal to a pitch of threads of the fasteners.

6. The system of claim 5, wherein each fastener of the plurality of threaded fasteners includes a head and a shaft, the shaft including a first threaded portion and a second threaded portion positioned between the first threaded portion and the head, wherein the second threaded portion has a greater diameter than the first threaded portion.

7. The system of claim 6, wherein the second threaded portion has a larger lead than the first threaded portion.

8. The system of claim 6, wherein the second threaded portion has at least twice the lead as the first threaded portion.

9. The system of claim 6, wherein the threads of the second threaded portion have larger major and minor diameters than the threads of the first threaded portion.

10. The system of claim 9, wherein each fastener of the plurality of fasteners includes an annular locking groove disposed between the head and the second threaded portion.

11. The system of claim 10, wherein an innermost peripheral edge of each opening of the plurality of openings is configured to be received in the annular locking groove.

12. The system of claim 1, wherein each opening of the plurality of openings includes a chamfered surface extending around a periphery thereof.

13. An intermaxillary fixation assembly comprising:
    first and second contourable plates each having a main body and a plurality of hooks, the main body having a length extending along a longitudinal axis between first and second ends, the main body being deformable into an arch shape corresponding to a shape of a maxilla or a mandible of a patient,
    the main body having a plurality of sections each having a section length extending parallel to the length of the main body, top and bottom edges defining a first width, and a plurality of openings that are oblong and are disposed between the top and bottom edges of each section of the plurality of sections and extending through a thickness of the main body, wherein the plurality of openings are positioned side-by-side along an axis that is parallel to the longitudinal axis of the main body,
    the main body including a plurality of recessed portions defining a second width smaller than the first width and disposed between adjacent sections of the plurality of sections,
    wherein each section of the plurality of sections is positioned between adjacent recessed portions of the plurality of recessed portions, each of the plurality of hooks extending from a corresponding section of the plurality of sections, each hook of the plurality of hooks extending from the bottom edge of the corresponding section to a hook terminal edge, wherein the terminal hook edge is positioned below the plurality of openings, wherein each section of the plurality of sections includes a support strut positioned between the plurality of openings;

a plurality of threaded fasteners adapted to threadably engage the plurality of openings and secure the first and second plates to the maxilla and the mandible, respectively; and at least one wire adapted to be attached to at least one hook of the plurality of hooks of the first plate and at least one hook of the plurality of hooks of the second plate.

14. The intermaxillary fixation assembly of claim 13, wherein each fastener of the plurality of fasteners includes a head and a shaft having a first threaded portion and a second threaded portion, the first threaded portion having threads with a smaller lead than threads of the second threaded portion.

15. The intermaxillary fixation assembly of claim 13, wherein each hook of the plurality of hooks includes a stem portion, a hooked lip and an elongated leg extending between the stem portion and the hooked lip, wherein the stem portion of each hook of the plurality of hooks is disposed at an angle relative to a corresponding leg and the main body of a corresponding one of the first and second plates.

16. An intermaxillary system comprising:

an elongated, contourable bar defining a longitudinal axis, the elongated, contourable bar including:

a plurality of mounting tabs, each mounting tab of the plurality of mounting tabs including a pair of elongated apertures separated from each other by a support strut, wherein the pair of elongated apertures are positioned next to each other along a length of the mounting tab extending parallel to the longitudinal axis, wherein each mounting tab of the plurality of mounting tabs is spaced apart from each other; and at least one hook positioned beneath each of the plurality of mounting tabs; and a plurality of fasteners configured to be received in the elongated apertures, each fastener of the plurality of fasteners includes a head and a shaft having a first threaded portion and a second threaded portion positioned between the first threaded portion and the head, the first threaded portion having a smaller diameter than the second threaded portion.

17. The intermaxillary fixation assembly of claim 16, wherein each fastener of the plurality of fasteners includes an annular locking groove disposed between the head and the second threaded portion, and wherein the second threaded portion is disposed between the head and the first threaded portion.

18. The intermaxillary fixation assembly of claim 17, wherein an innermost peripheral edge of each elongated aperture of the plurality of elongated apertures is configured to be received in the annular locking groove.

19. The intermaxillary fixation assembly of claim 16, wherein the threads of the second threaded portion have a larger diameter than threads of the first threaded portion.

20. The intermaxillary fixation assembly of claim 16, wherein each elongated aperture of the pair of elongated apertures includes a chamfered surface extending around a periphery thereof.

21. The intermaxillary fixation assembly of claim 16, wherein each hook of the plurality of hooks includes a stem that extends from the elongated, contourable bar in a first direction, and wherein each mounting tab of the plurality of mounting tabs extends from the elongated, contourable bar in a second direction opposite the first direction.

22. The intermaxillary fixation assembly of claim 16, further comprising at least one wire and another elongated, contourable bar having a plurality of openings and a plurality of hooks, the at least one wire engaging at least one of the hooks of each of the elongated, contourable bars.

23. The medical device of claim 16, wherein each fastener of the plurality of fasteners has a tapered tip extending distally from the first threaded portion.

* * * * *